United States Patent
Dutartre et al.

(10) Patent No.: US 6,238,941 B1
(45) Date of Patent: May 29, 2001

(54) CHARACTERIZING OF SILICON-GERMANIUM AREAS ON SILICON

(75) Inventors: Didier Dutartre, Meylan; Jean-Claude Oberlin, Le Touvet, both of (FR)

(73) Assignee: STMicroelectronics S.A., Gentilly (FR)

( * ) Notice: Subject to any disclaimer, the term of this patent is extended or adjusted under 35 U.S.C. 154(b) by 0 days.

(21) Appl. No.: 09/652,682

(22) Filed: Aug. 31, 2000

(30) Foreign Application Priority Data

Sep. 2, 1999 (FR) .................................................. 99 11142

(51) Int. Cl.⁷ .................................................. H01L 21/66
(52) U.S. Cl. .................................. 438/14; 378/73; 378/72
(58) Field of Search .................................. 438/14; 378/73, 378/72

(56) References Cited

U.S. PATENT DOCUMENTS

| | | | |
|---|---|---|---|
| 5,442,676 | * 8/1995 | Fewster | 378/72 |
| 5,530,732 | 6/1996 | Takemi | 378/73 |
| 6,081,579 | * 6/2000 | Nagano et al. | 378/73 |

OTHER PUBLICATIONS

French Search Report from French Patent Application No. 99/11142, filed Sep. 2, 1999.
Christ T., et al.: "Analysis Of Light Emitting Diodes By X–Ray Reflectivity Measurements", Thin Solid Films, Ch, Elsevier–Sequoia S.A. Lausanne, vol. 302, No. 1–2, Jun. 20, 1997, pp. 214–222.

* cited by examiner

*Primary Examiner*—John F. Niebling
*Assistant Examiner*—Olivia Luk
(74) *Attorney, Agent, or Firm*—Wolf, Greenfield & Sacks, P.C.; James H. Morris; Theodore E. Galanthay

(57) ABSTRACT

A method for characterizing a structure including single-crystal silicon-germanium areas on a single-crystal silicon substrate, including the steps of measuring the X-ray diffraction spectrum of the structure, simulating the diffraction spectrum of a single-crystal silicon substrate, simulating the diffraction spectrum of a single-crystal silicon substrate entirely coated with a single-crystal SiGe layer, adding the simulated spectrums while assigning them weights $\underline{a}$ and $\underline{1-a}$ to obtain a sum spectrum, comparing the sum spectrum with the measured spectrum and adjusting the simulation parameters and weight $\underline{a}$ to reduce the distance between the sum spectrum and the measured spectrum, and after optimizing, adopting the simulation parameters as the measurement parameters.

3 Claims, 2 Drawing Sheets

CHARACTERIZING OF SILICON-GERMANIUM AREAS ON SILICON

BACKGROUND OF THE INVENTION

1. Field of the Invention

The present invention relates to a method for characterizing silicon-germanium areas obtained by epitaxial growth on portions of a single-crystal silicon substrate.

2. Discussion of the Related Art

There exists a growing tendency in microelectronics to use areas of a silicon-germanium heterocrystal ($Si_xGe_{1-x}$) obtained by epitaxial growth on surface portions of a silicon substrate, the other portions of which are masked. Such $Si_xGe_{1-x}$ areas are used, in particular, as a base for bipolar transistors to obtain improved speed characteristics and provide devices with good radiofrequency performance.

SUMMARY OF THE INVENTION

The present invention provides a novel method in which, rather than trying to adjust a measured curve, a distinct model is used. The present invention provides for linearly combining a model corresponding to a single-crystal silicon substrate alone with a conventional model corresponding to the superposition of a uniform SiGe layer on a silicon substrate. These models are combined by assigning a weight to the model corresponding to the complex structure, this weighting factor substantially corresponding to the surface ratio between the surface occupied by the single-crystal SiGe regions and the total layer surface.

More specifically, the present invention provides a method for characterizing a structure including single-crystal silicon-germanium areas on a single-crystal silicon substrate, including the steps of:

measuring the X-ray diffraction spectrum of the structure, simulating the diffraction spectrum of a single-crystal silicon substrate, simulating the diffraction spectrum of a single-crystal silicon substrate entirely coated with a single-crystal SiGe layer, adding the simulated spectrums while assigning them weights $a$ and $1-a$ to obtain a sum spectrum, comparing the sum spectrum with the measured spectrum and adjusting the simulation parameters and weight $a$ to reduce the distance between the sum spectrum and the measured spectrum, after optimizing, adopting the simulation parameters as the measurement parameters.

According to an embodiment of the present invention, weight $a$ is chosen at an initial value, before optimizing, which is substantially equal to the ratio between the surface area occupied by the SiGe areas and the total surface area of a silicon wafer.

BRIEF DESCRIPTION OF THE DRAWINGS

In the following description, references will be made to the accompanying drawings, among which.

DETAILED DESCRIPTION

Figure 1:
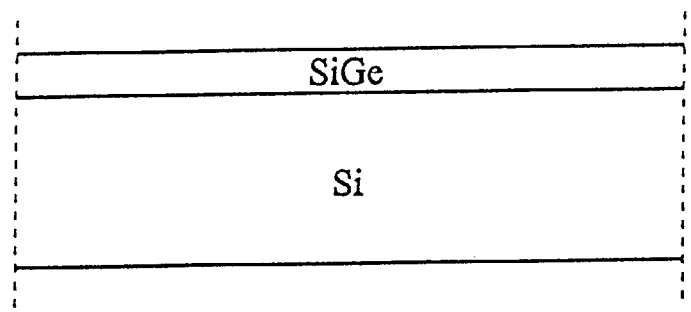
FIG. 1 is a cross-section view of a SiGe layer on a silicon substrate.
Figure 2A:
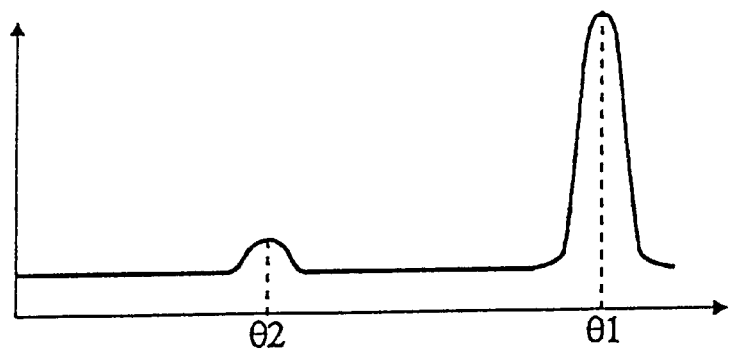
FIG. 2A very schematically shows an X-ray diffraction spectrum of the structure of FIG. 1.
Figure 2B:
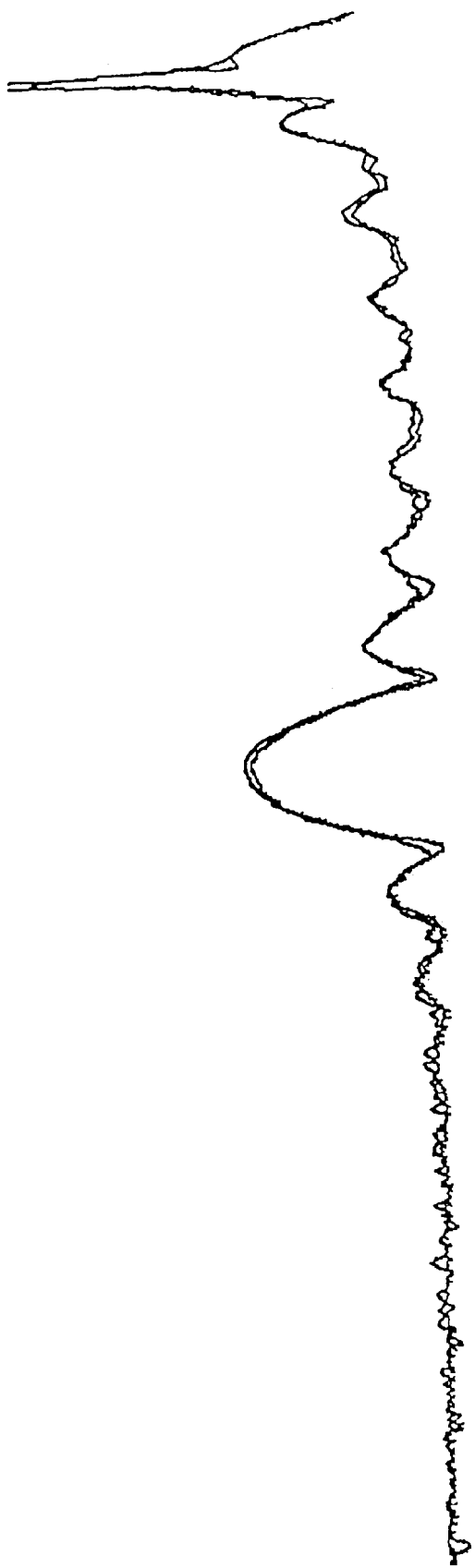
FIG. 2B shows a real example of X-ray diffraction spectra measured and simulated for the structure of FIG. 1.

To determine the characteristics of a uniform $Si_xGe_{1-x}$ layer deposited on a silicon substrate, such as shown in FIG. 1, it is known to use X-ray diffraction methods. For this purpose, a beam of monochromatic X-rays is projected on the sample surface. As shown in FIG. 2A, the reflected intensity according to the angle of incidence and/or emergence especially includes a main diffraction peak for an angle $\theta1$ corresponding to the single-crystal silicon substrate and a second significant diffraction peak for an angle $\theta2$ corresponding to the distance between reticular planes of the silicon-germanium heterocrystal, which especially provides an indication about proportion x in expression $Si_xGe_{1-x}$. In reality, the obtained diffraction spectrum is more complex, as shown by the curve of FIG. 2B, and in particular includes a number of secondary peaks. The position and intensity of the main peaks and of the secondary peaks provide information on the composition, the thickness, the surface state, and the roughness of the silicon substrate and of the $Si_xGe_{1-x}$ layer.

More specifically, a preferred method to determine the characteristics of the structure based on its diffraction spectrum uses a modeling. This method is for example implemented in characterization device DCD2 of Philips Analytical Company, which uses as a modeling program a so-called Epitaxy program and as a comparison-optimization program a so-called SmoothFit program. This method consists of establishing by a mathematical calculation a model of the diffraction spectrum that should be obtained for a supposed $Si_xGe_{1-x}$ structure on a silicon substrate substantially having the desired characteristics. Then, the model is compared with the measured spectrum and the structure parameters introduced in the model are adjusted by any known minimizing method to obtain as good a correspondence as possible between the measured spectrum and the model. In FIG. 2B, the two spectrums at the final stage of this process have been indicated. In FIG. 2B, the model corresponds to the smoothest curve. Of course, the calculations and comparisons are performed from digitized data corresponding to the above-mentioned curves.

Once the optimization is obtained, the model parameters are the parameters characterizing the analyzed structure.

This method of modeling and optimizing in relation with uniform SiGe layers on a silicon substrate provides good results and the deposited layers can be efficiently characterized.

Figure 3:
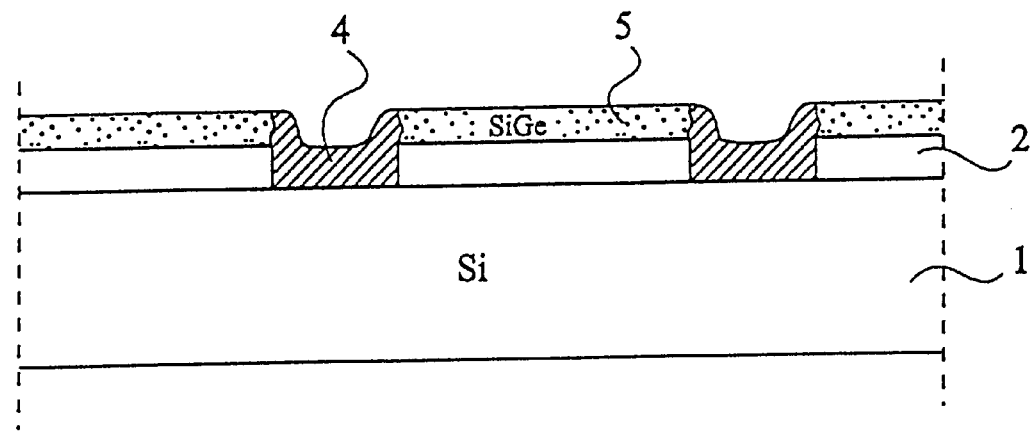
FIG. 3 is a cross-section view of single-crystal portions of an SiGe layer on a silicon substrate.

However, a problem is raised with structures of the type shown in FIG. 3. On a single-crystal silicon substrate is formed a structure of layers 2 including one or several layers, for example thick oxide coated with polysilicon, polysilicon, or an assembly of polysilicon, silicon oxide, and silicon nitride layers. Openings are formed in layer(s) 2 to reach substrate 1, then $Si_xGe_{1-x}$ is epitaxially grown. As a result, above the openings reaching the single-crystal silicon, single-crystal $Si_xGe_{1-x}$ areas 4 are obtained. According to the growth method, this growth is localized, or multiple-crystal or amorphous $Si_xGe_{1-x}$ 5 is obtained above layers 2. In an X-ray diffraction analysis, only single-crystal SiGe areas 4 and single-crystal silicon substrate 1 will have a diffracting effect, the multiple-crystal or amorphous layers having no effect on the X-ray diffraction.

Experience has shown that the X-ray spectrums made from such structures and exploited by the usual modeling/optimization method provide poor results and do not enable a good characterization of limited $Si_xGe_{1-x}$ areas. This is due to the fact that the silicon diffraction peak at angle $\theta1$ becomes extremely large with respect to the other peaks that are drowned in noise, and especially the secondary peaks neighboring the peak associated with silicon are not properly exploited.

To solve this problem, various solutions have been envisaged. A first solution, which is essentially mathematical, consists, before comparing the measured curve with the model, of modifying the measured spectrum to limit the height and width of the peak associated with silicon. However, this method does not provide satisfactory results, especially due to the fact that the secondary diffraction peaks masked by the main diffraction peak associated with silicon cannot be satisfactorily reconstructed.

Another approach to solve this problem consists of performing an X-ray diffraction measurement on the silicon substrate before the epitaxy deposition of the SiGe layer, then linearly combining the spectrum corresponding to the general structure with the spectrum corresponding to silicon. Again, this does not provide satisfactory results since it is very difficult in practice to align two successive measured spectrums and the measurement of the peak corresponding to the substrate, which is very intense and very narrow, seems to be altered by the actual measurement and by any disturbance of the substrate (even very slight) due to its anneal or to the SiGe deposition.

Thus, in the case where only localized areas of single-crystal SiGe are formed, present programs do not correctly process the entire spectrum, which provides erratic results. The results especially depend on the initialization values of the parameters and may diverge.

The present invention provides a novel method in which, rather than trying to adjust a measured curve, a distinct model is used. The present invention provides for linearly combining a model corresponding to a single-crystal silicon substrate alone with a conventional model corresponding to the superposition of a uniform SiGe layer on a silicon substrate. These models are combined by assigning a weight to the model corresponding to the complex structure, this weighting factor substantially corresponding to the surface ratio between the surface occupied by the single-crystal SiGe regions and the total layer surface.

More specifically, the present invention provides a method for characterizing a structure including single-crystal silicon-germanium areas on a single-crystal silicon substrate, including the steps of:

measuring the X-ray diffraction spectrum of the structure, simulating the diffraction spectrum of a single-crystal silicon substrate, simulating the diffraction spectrum of a single-crystal silicon substrate entirely coated with a single-crystal SiGe layer, adding the simulated spectrums while assigning them weights $a$ and $1-a$ to obtain a sum spectrum, comparing the sum spectrum with the measured spectrum and adjusting the simulation parameters and weight $a$ to reduce the distance between the sum spectrum and the measured spectrum, after optimizing, adopting the simulation parameters as the measurement parameters.

According to an embodiment of the present invention, weight $a$ is chosen at an initial value, before optimizing, which is substantially equal to the ratio between the surface area occupied by the SiGe areas and the total surface area of a silicon wafer.

Of course, the present invention is likely to have various alterations, modifications, and improvements which will readily occur to those skilled in the art. In particular, a model is conventionally provided for the case where the SiGe layer is then coated with a silicon layer. This case may occur in practice when silicon emitter areas have been formed above the base SiGe areas. The present invention also applies to the case where the SiGe profile is complex and/or different SiGe layers are present, the simulated model then corresponding to such a structure.

Such alterations, modifications, and improvements are intended to be part of this disclosure, and are intended to be within the spirit and the scope of the present invention. Accordingly, the foregoing description is by way of example only and is not intended to be limiting. The present invention is limited only as defined in the following claims and the equivalents thereto.

What is claimed is:

1. A method for characterizing a structure including single-crystal silicon-germanium areas on a single-crystal silicon substrate, including the steps of:

measuring the X-ray diffraction spectrum of the structure, simulating the diffraction spectrum of a single-crystal silicon substrate, simulating the diffraction spectrum of a single-crystal silicon substrate entirely coated with a single-crystal SiGe layer, adding the simulated spectrums while assigning them weights $a$ and $1-a$ to obtain a sum spectrum, comparing the sum spectrum with the measured spectrum and adjusting the simulation parameters and weight $a$ to reduce the distance between the sum spectrum and the measured spectrum, after optimizing, adopting the simulation parameters as the measurement parameters.

2. The method of claim 1, wherein weight a is chosen at an initial value, before optimizing, which is substantially equal to the ratio between the surface area occupied by the SiGe areas and the total surface area in the measurement area.

3. The method of claim 1, wherein the SiGe layer is coated with $a$ silicon layer and wherein the simulated model corresponds to such a structure.

* * * * *